(12) United States Patent
Hamada

(10) Patent No.: US 7,318,817 B2
(45) Date of Patent: Jan. 15, 2008

(54) MINIMAL ACCESS LUMBAR DISKECTOMY INSTRUMENTATION AND METHOD

(75) Inventor: James S. Hamada, Manhattan Beach, CA (US)

(73) Assignee: K2M, Inc., Leesburg, VA (US)

( * ) Notice: Subject to any disclaimer, the term of this patent is extended or adjusted under 35 U.S.C. 154(b) by 577 days.

(21) Appl. No.: 11/001,628

(22) Filed: Nov. 30, 2004

(65) Prior Publication Data

US 2005/0101985 A1    May 12, 2005

Related U.S. Application Data

(63) Continuation-in-part of application No. 10/280,624, filed on Oct. 25, 2002, now Pat. No. 6,849,064.

(51) Int. Cl.
*A61M 5/178* (2006.01)

(52) U.S. Cl. .............. 604/164.01; 604/164.05

(58) Field of Classification Search ........... 604/164.01, 604/164.03, 164.04, 164.05, 164.1, 164.11, 604/164.12, 264; 606/184, 185, 205
See application file for complete search history.

(56) References Cited

U.S. PATENT DOCUMENTS

| 3,750,652 | A | * | 8/1973 | Sherwin | ............... | 606/90 |
| 5,667,520 | A | * | 9/1997 | Bonutti | ............... | 606/190 |
| 5,707,362 | A | | 1/1998 | Yoon | | |
| 6,743,206 | B1 | | 6/2004 | Smith et al. | | |
| 6,767,355 | B2 | | 7/2004 | Frova et al. | | |

OTHER PUBLICATIONS

Aldrich F: Posterolateral microdiscectomy for cervical monoradicujopathy caused by posterolateral soft cervical disc sequestration. J. Neurosurg 72: 370-377, 1990.
Aronson N: The management of soft cervical disc protrusions using the Smith-Robinson approach. Clinical Neurosurgery 20:253-258, 1973.
Caspar W: A new surgical procedure for lumbar disc herniation causing less tissue damage through a microsurgical approach. Adv Neurosurg 4:72-80, 1977.
Cloward RB: The anterior approach for removal of ruptured cervical disks. J Neurosurg 15:602-617, 1958.
Fessler, RG, '(boo, Larry: Minimally Invasive Cervical Microendoscopic Foraminotomy: An Initial Clincal Experience. Neurosurg 51:37-452002.

(Continued)

*Primary Examiner*—Kevin T. Truong
(74) *Attorney, Agent, or Firm*—Carter, DeLuca, Farrell & Schmidt, LLP

(57) ABSTRACT

A minimal incision maximal access system allows for maximum desirable exposure along with maximum access to the operative field utilizing a minimum incision as small as the METRx and Endius systems. Instead of multiple insertions of dilating tubes the design is is a streamlined single entry device to avoid repetitive skin surface entry. The system offers the capability to expand to optimum exposure size for the surgery utilizing hinged bi-hemispherical or oval working tubes applied over an introducer obturator which is controllably dilated to slowly separate muscle tissue. Deeper end working and visualization areas with maximum proximal access and work dimensions are provided to makes the operative procedure safer in application and shorten the surgeons's learning curve because it most closely approximates the ability to use open microdiskectomy techniques.

9 Claims, 13 Drawing Sheets

OTHER PUBLICATIONS

Fessler RG, Guiot BH, 'boo LT: A minimally invasive technique for decompression of the lumbar spine. Spine 27:432-438, 2002.

Foley KT, Smith MM: Microendoscopic discectomy. Tech Neurosurgery 3: 301-307, 1997.

Henderson CM, Hennessy RG, Shuey HJ, Shackelford EG: Posterior-lateral foraminotomy as an exclusive operative technique for cervical radiculopathy: A review of 846 consecutively operated cases. Neurosurgery 13: 504-521, 1983.

Hermantin FU, Peters T, Quartararo L, Kambin P: A prospective, randomized study comparing the results of open discectomy with those of video-assisted arthroscopic microdiscectomy. I Bone Joint Surge Am S1A:958-965, 1999.

Kawaguchi Y, Matsui H, Gejo R, Tsuji H: Back muscle injury after posterior lumbar spine surgery: A histologic and enzymatic analysis. Spine 21:941-944, 1996.

Lin PM: Posterior lilmbar interbody fusion technique: Complications and pitfalls, Clinical Orthopedics 193:90-102, 1985.

Lin PM, Cautilli RA, Joyce MF: Posterior lumbar interbody fusion. Clinical Orthopedics 180:154-168, 1983.

Malis LI: Instrumentation and techniques in microsurgery. Clinical Neurosurgery 26:626-636, 1979.

Rantanen J, Hurme M, Falck B, Alaranta H, Nykvist F, Lebto M, Finoja S, Kalimo H: The lumbar multifidus muscle five years after surgery for a lumbar intervertebral disc herniation. Spine 18:568-574, 1993.

Rob SW, Kim DH, Cardoso AC, Fessier RG: Endoscopic foraminotomy using MED system in cadaveric specimens. Spine 25:260-264, 2000.

Sihvonen T, Herno A, Palijarva L, Airaksinen O, Partanen J, Tapaninaho A: Local denervation atrophy of paraspinal muscles in postoperative failed back syndrome. Spine 18:575-581, 1993.

StyflR, Willen J: The effects of external compression by three different retractors on pressure in the erector spine muscles during and after posterior lumbar spine surgery in humans. Spine 23:354-358, 1998.

Tsai RYC, Yang RS, Bray RS: Microscopic laminotomies for degenerative lumbar spinal stenosis. J Spinal Disord 11:389-394, 1998.

Weber BR, Grod D, Dvorak J, Muntener M: Posterior surgical approach to the lumbar spine and its effect on the multifidus muscle. Spine 22:1765-1772, 1992.

Weiner BK, Walker M, Brower RS, McCulloch JA: Microdecompression for lumbar spinal canal stenosis. Spine 24:2268-2272, 1999.

Endius: The Pioneer ofEndoscopic Spine Fusion Atavi System: Endoscopic Posterolateral Fusion (Internet Reference).

* cited by examiner

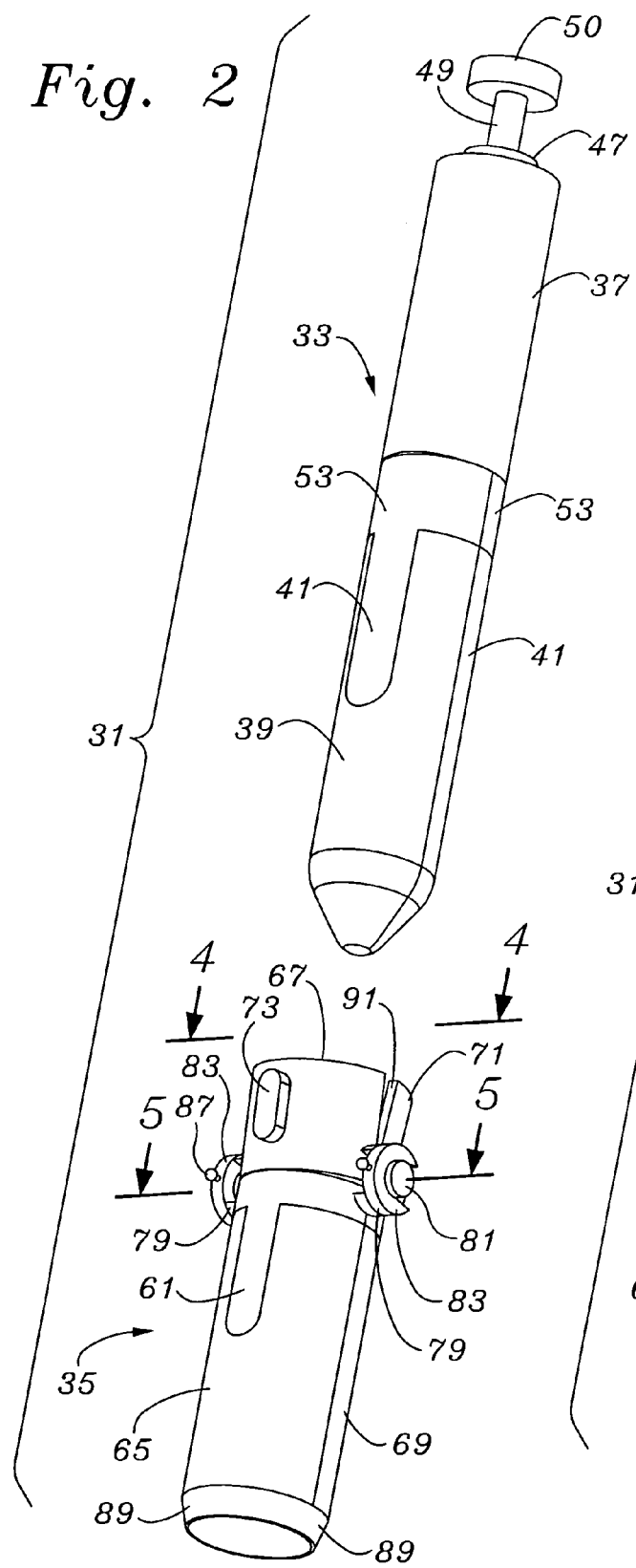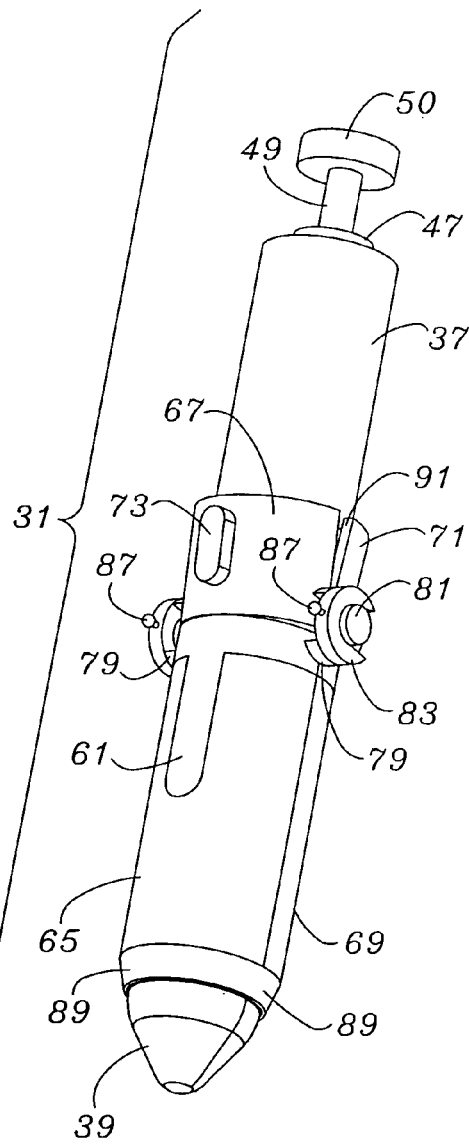

Fig. 17
Fig. 18
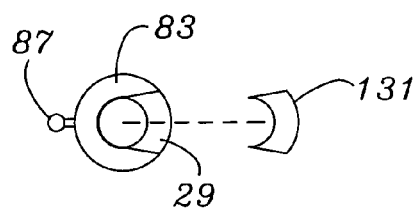
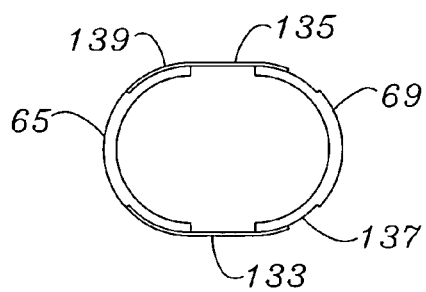
Fig. 15
Fig. 16
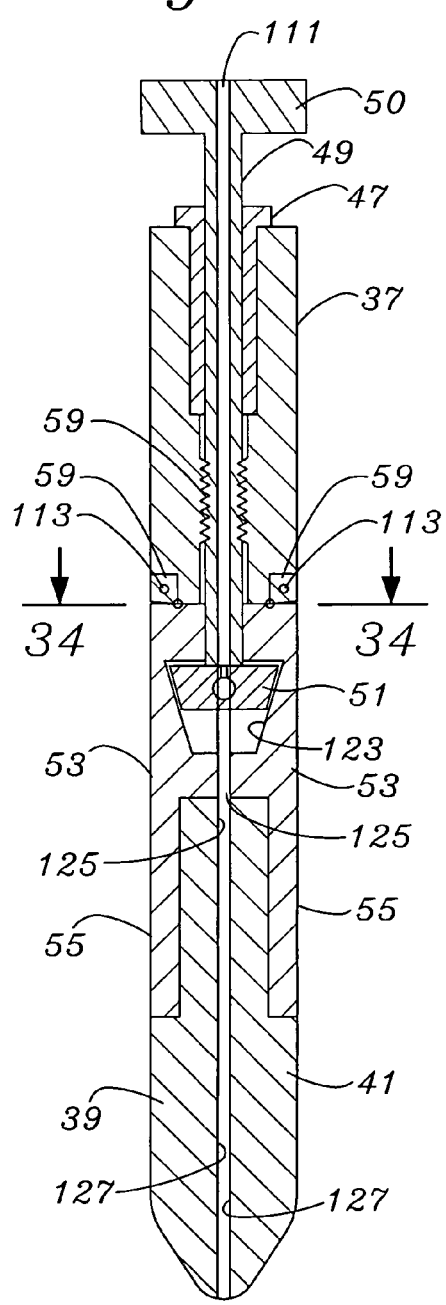
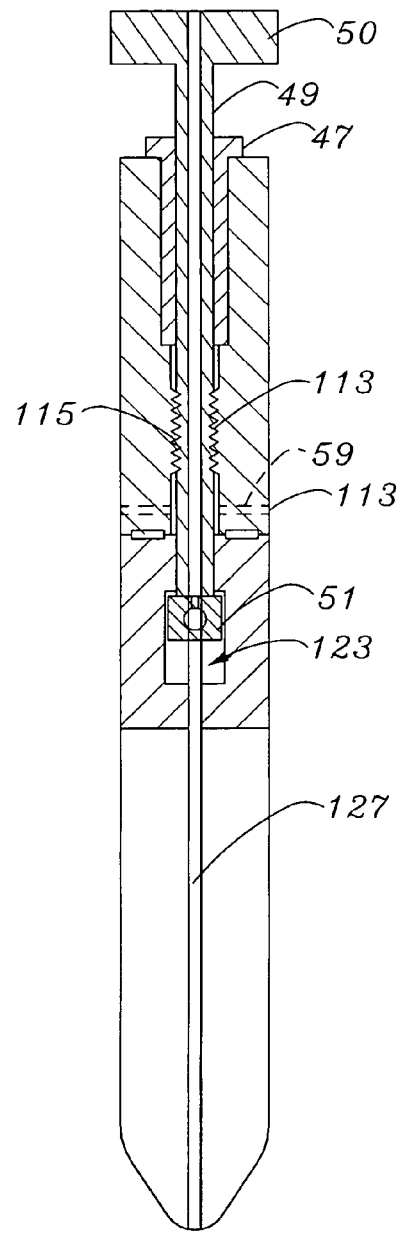

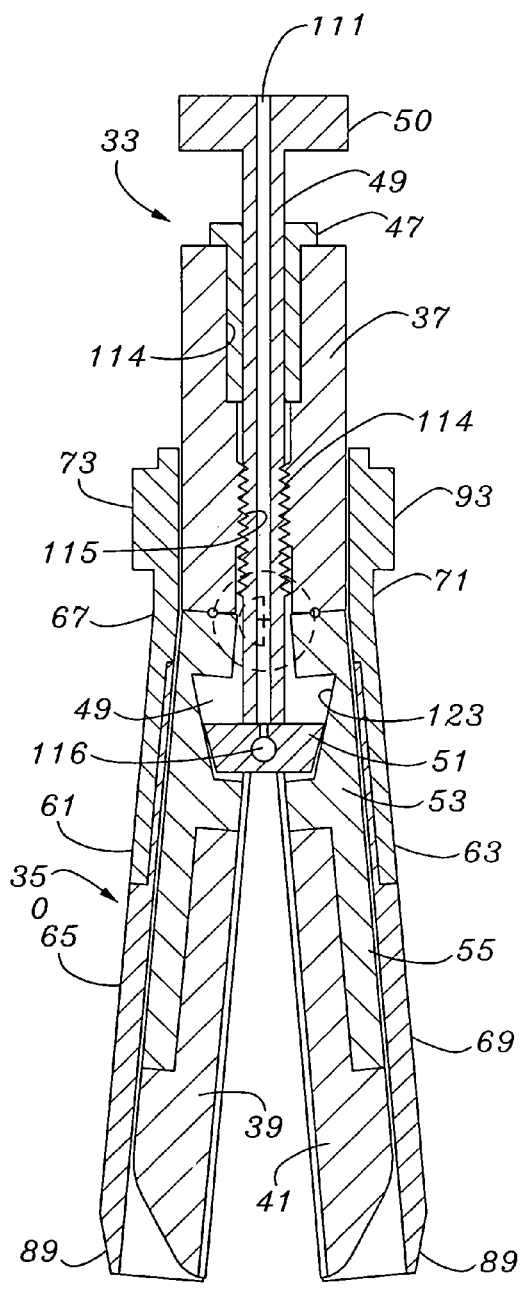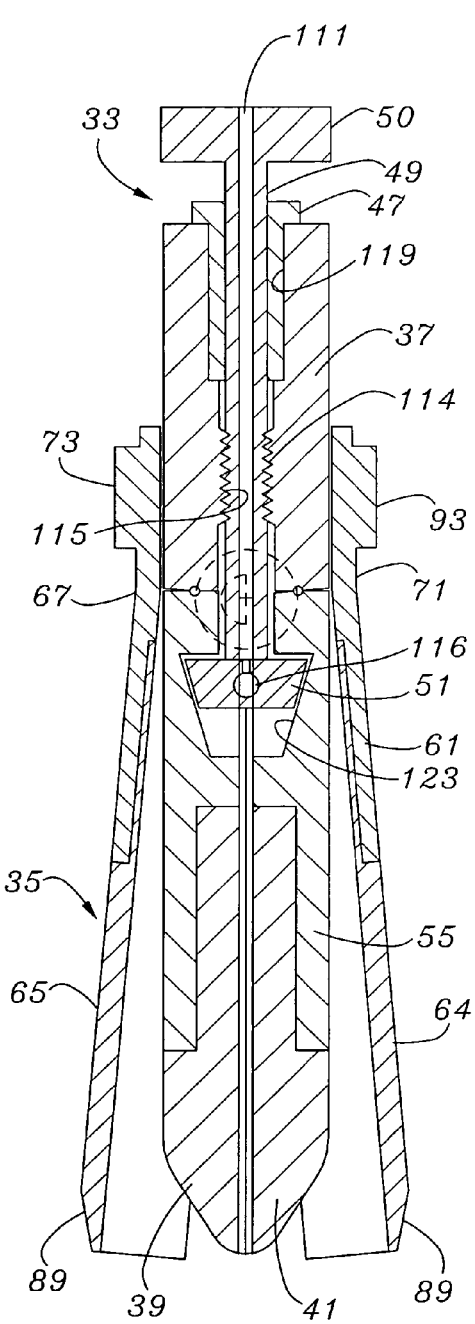

MINIMAL ACCESS LUMBAR DISKECTOMY INSTRUMENTATION AND METHOD

This is a continuation-in-part of U.S. patent application Ser. No. 10/280,624 filed Oct. 25, 2002 now U.S. Pat. No. 6,849,064.

FIELD OF THE INVENTION

The present invention relates to improvements in the field of minimal access lumbar posterior surgery and more particularly to instrumentation which allows for maximal access to the surgical field through the smallest possible incision. Greater access is allowed into the working field while enjoying the reduction of trauma and disturbance to surrounding tissues, which results in a reduced the time necessary to complete the operative procedure, increased safety of the procedure, and increased accuracy by providing an expanded working field.

BACKGROUND OF THE INVENTION

Microscopic Lumbar Diskectomy techniques were developed and championed by Dr. Robert Williams in the late 1970's and by Dr. John McCullough in the late 1980's and 1990's. For the first time since the advent of Lumbar Disc Surgery by Mixter and Barr in 1934 a method was introduced allowing Lumbar Disc Surgery to be performed through a small incision safely resulting in faster patient recovery and converting a two to five hospital stay procedure virtually to an outpatient procedure.

The special retractors developed by Drs. Williams and McCullough however were often difficult to maintain in optimum position and relied on the interspinous and supraspinatus ligaments for a counter fixation point severely stretching the structures. This stretching along with the effects of partial facetomy, diskectomy, removal of the ligamentum flavum and posterior longitudinal ligament contributed to the development of Post Diskectomy Instability. Taylor retractors were also used but were cumbersome, required larger incisions and often injured the facet joints.

Dr. William Foley in 1997 introduced a tubular system mated to an endoscope which he labeled a Minimal Endoscopic Diskectomy (MED) system. It featured sequentially dilating the Lumbar Paraspinous Muscles allowing a working channel to be advanced down to the level of operation through which nerve root decompression and Diskectomy Surgery could be performed with a small incision and less muscle trauma. Improvements were made by Dr. Foley in his second generation METRx system. However, there were several disadvantages to the MED and METRx systems.

In the MED and METRx systems, the cylindrical working channel considerably restricted visualization and passage of instruments. It also compromised the "angle of approach" necessary for safe usage of the operating instruments. This problem was proportionately aggravated with the long length of the tube. This compromised visualization contributed to the following problems, including nerve injury, dural tear, missed disc fragments, inadequate decompression of the lateral recess, increased epidural bleeding, difficulty controlling epidural bleeding, inadequate visualization of the neuroforamen, and inadequate decompression of neuroforamen.

The repetitive introduction of successively larger dilators caused skin abrasion with the potential for carrying superficial skin organisms down to the deeper tissue layers hypothetically increasing the risk of infection. The learning curve for operating in a two dimension endoscopic field proved to be arduous and contributed to the above complications.

The attempted use of the METRx system for more complex procedures such as fusion was further hazardous by inherent limitations.

Endius in September of 2000 then introduced a similar device which differed by having an expandable foot piece to allow greater coverage of the operative field. However, the enlarged foot piece was unwieldy and difficult to seat properly. Exposure of the angle of approach was also limited by having to operate through a proximal cylindrical tube with its limitations as described before. In comparison to the METRx system the working area was improved but access was again restricted by the smaller proximal cylinder.

Both systems offered endoscopic capability but many spine surgeons chose to use an operating microscope or loupes to maintain 3-Dimensional visualization rather than the depth impaired 2-Dimensional endoscopic presentation. Keeping debris off of the endoscopic lens has also proved to be a troubling challenge.

SUMMARY OF THE INVENTION

The system and method of the invention, hereinafter minimal incision maximal access system, includes a surgical operating system that allows for maximum desirable exposure along with maximum access to the operative field utilizing a minimum incision as small as the METRx and Endius systems. The minimal incision maximal access system disclosed offers advantages over the METRx and Endius systems in several respects. First, instead of multiple insertions of Dilating Tubes the Invention is a streamlined single entry device. This avoids repetitive skin surface entry. Second, the minimal incision maximal access system offers the capability to expand to optimum exposure size for the surgery utilizing hinged bi-hemispherical or oval Working Tubes applied over an introducer Obturator which is controllably dilated to slowly separate muscle tissue.

Third, the minimal incision maximal access system maximizes deeper end working and visualization area with maximum proximal access and work dimensions significantly greater than either the METRx or Endius devices and methods. Fourth, the minimal incision maximal access system provides expanded visual and working field to makes the operative procedure safer in application and shorten the surgeons's learning curve because it most closely approximates the open microdiskectomy techniques. Fifthly, the minimal incision maximal access system has a tapered ended Obturator which allows for tissue spread rather than muscle tissue tear and subsequent necrosis.

Sixth, the minimal incision maximal access system controls muscle oozing into the operative field which is controlled by simply opening the tubes further. This also thereby controls the bleeding by pressure to the surrounding tissues. Seventh, in contrast to the cylindrical tube based systems such as the METRx and Endius the minimal incision maximal access system offers a larger working area in proportion to the working depth. For the first time this allows for a minimal access technique to be applied to the large or obese patients. The enlarged footprint of the longer tubes in the minimal incision maximal access system is a major difference from any other minimal access system.

An eighth advantage of the minimal incision maximal access system is that ist expandable design allows for excellent exposure for more complex procedures such as fusion and instrumentation including TLIF, PLIF, and TFIF (Transfacet Interbody Fusion), as well as allowing application for anterolateral lumbar disc surgery. The minimal incision maximal access system can also be used for cervical surgery posteriorly (foraminotomy, lateral mass instrumented fusion) as well as anterior cervical diskectomy and fusion. The minimal incision maximal access system can also be used for anterior lumbar interbody fusion be it retroperitoneal, transperitoneal or laparoscopic.

A ninth advantage of the minimal incision maximal access system is that the medial oval cutout of the retractors, or sleeve forming the working tube, allows more central docking on the spine which is problematic for other devices. A medialized docking provides access for easier and better and safer dural retraction to address midline pathology. A tenth advantage is had by including an anti-reflective inner surface of the retractor sleeves which eliminates unwanted glare.

An eleventh advantage of the minimal incision maximal access system includes the slanted and contoured distal end of the retractor sleeve which allows minimal resistance for entry and advancement to the docking site. A twelfth advantage minimal incision maximal access system is the provision of a variety of retractor tips specific for different surgical procedures.

A thirteenth advantage of the minimal incision maximal access system is the provision of oval retractor sleeves for larger access requirements such as pedicle to pedicle exposure and especially in the case where pedicle screw instrumentation is to be applied. This minimizes unnecessary muscle spread by providing a smaller waist profile than a circular system. A fourteenth advantage of the minimal incision maximal access system is that the larger retractor sleeve also features one or two "skirts" to cover the lateral aperture created by the spread of the two retractor sleeves when opened. This prevents soft tissue and muscle ingress into the working cone. The skirts are attached to the working tube either at the hinge or on one of the two halves of the sleeve.

A fifteenth advantage of the minimal incision maximal access system is the provision of a modular design in which the retractor sleeves can be quickly removed, changed and reapplied. In this version the proximal port can also be modular and changeable to fit the needs of a specific surgical procedure. A sixteenth advantage of the minimal incision maximal access system is that the retractor sleeves can be made out of metal, ceramic or plastic, can be opaque or translucent, and can have tips of different shapes for different applications. A seventeenth advantage is the provision of snap lock connections of the major parts of the Invention provides for easy assembly and disengagement for cleaning and sterilization purposes.

Further, the Obturator is cannulated for carrying a central Guide Pin Passage. It has a Handle component which remains superficial to the skin. The obturator houses an internal hinge device which allows for spread of the two obturator tips.

BRIEF DESCRIPTION OF THE DRAWINGS

The invention, its configuration, construction, and operation will be best further described in the following detailed description, taken in conjunction with the accompanying drawings in which:

FIG. 2 is a perspective assembled view illustrating the relative positions of the obturator and working tube;

FIG. 3 is a perspective assembled view illustrates the position of the obturator after it has been inserted into the working tube;

FIG. 15 is a sectional view taken along line 14-14 of FIG. 12 and gives a sectional view from the same perspective seen in FIG. 14;

FIG. 16 is a view of the obturator similar to that seen in FIG. 15, but turned ninety degrees along its axis and illustrates the wedge as having a narrower dimension to lend internal stability;

FIG. 17 is a closeup view of the external hinge assembly seen in FIG. 1 and illustrates the optional use of a plug to cover the exposed side of a circular protrusion;

FIG. 18 is a view taken along line 18-18 of FIG. 11 and illustrates the use of an optional skirt having flexible members which spread from an initial curled position to a straightened position to better isolate the surgical field;

FIG. 32 is a sectional view of the obturator of FIG. 1 within the working tube of FIG. 1 with the wedge 51 seen at the bottom of an internal wedge conforming space;

FIG. 33 illustrates the obturator seen in FIG. 32 as returned to its collapsed state.

DETAILED DESCRIPTION OF THE PREFERRED EMBODIMENT

Figure 1:
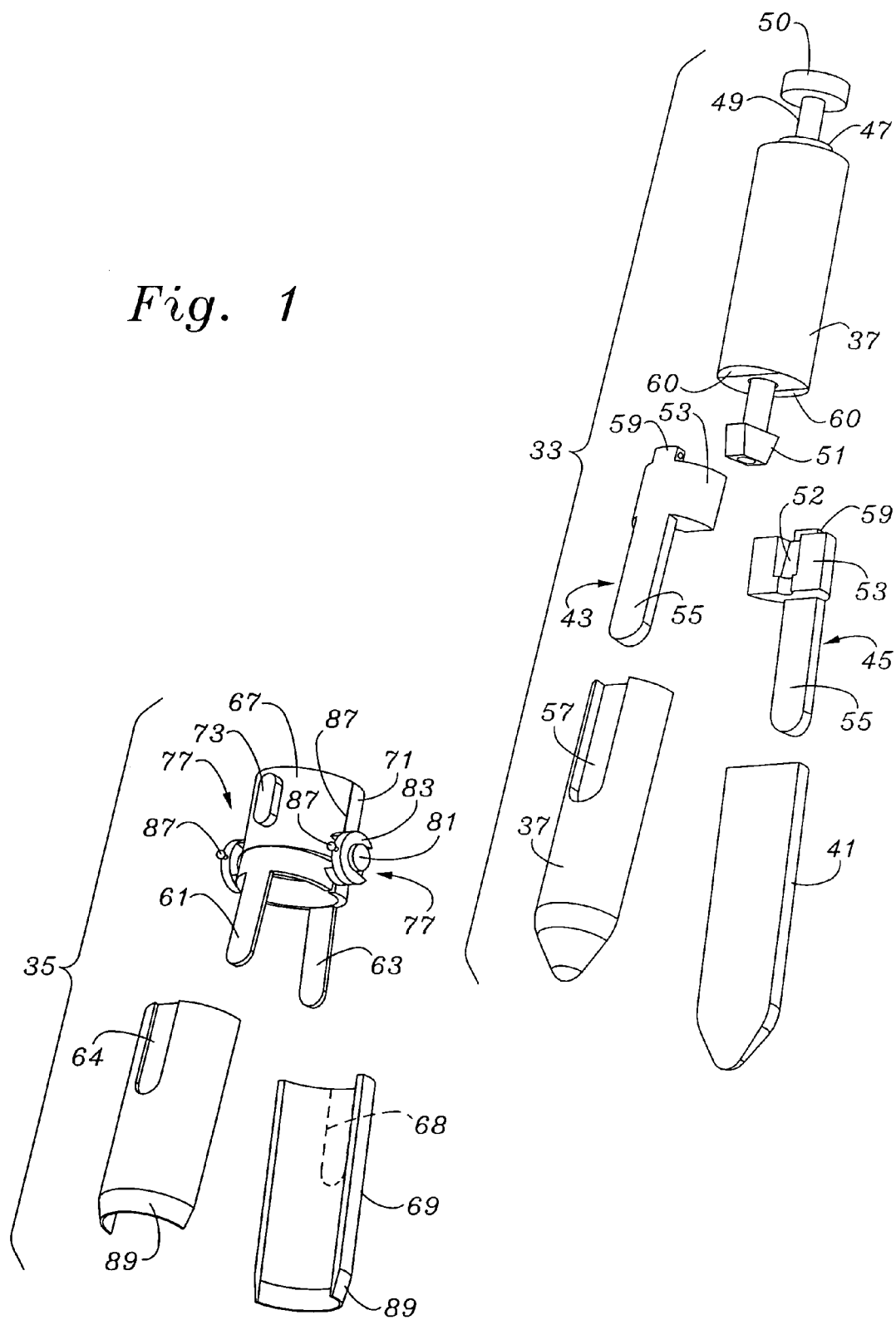
FIG. 1 is a perspective view of a working tube with an angled upper section and shown in position with respect to an obturator insertable into and workable within the working tube.

The description and operation of the minimal incision maximal access system will be best described with reference to FIG. 1 and identifying a general system 31. System 31 includes an obturator 33 and a working tube 35. The orientation of the obturator 33 is in a slightly displaced from a position of alignment with the working tube 35 for entry into working tube 35 and to provide the initial carefully controlled force for spreading the working tube 35, as will be shown.

Obturator includes an upper control housing 37 and a pair of spreading legs 39 and 41. The spreading legs 39 and 41 are seen as coming together to form a conical tip and thus have hemi conical end portions. The spreading legs 39 and 41 overfit attachment leg portions 43 and 45, respectively. At the top of the upper control housing 37 a boss 47 surrounds and supports the extension of a control shaft 49. A knurled thumb knob 50 sits atop the control shaft 49 to facilitate controlled turning of the control shaft 49 to control the degree of spreading of the spreading legs 39 and 41. Thus spreading can be controlled independently of pressure applied along the length of the obturator 33.

Below the upper control housing 37 is the bottom of the control shaft 49 which operates against a wedge 51. The wedge 51 operates within a pair of opposing slots 52 in an upper portion 53 of the overfit attachment leg portions 43 and 45. The lower ends of the overfit attachment leg portions 43 and 45 include insertion tangs 55 which fit within insertion slots 57 of the spreading legs 39 and 41. The overfit attachment leg portions 43 and 45 are pivotally attached to the upper control housing 37 internally by pivot blocks 59 which fit within access apertures 60.

The working tube 35 has a first lower extending connection tang 61 and a second lower extending connection tang 63. First lower extending connection tang 61 connects into a slot 64 of a lower tube hemicylindrical portion 65. The first lower extending connection tang 61 is fixed to an upper angled hemicylindrical portion 67. The second lower extending connection tang 63 connects into a slot 68 of a lower tube hemicylindrical portion 69. Second lower extending connection tang 61 is fixed to and an upper angled hemicylindrical portion 71. The upper angled hemicylindrical portion 67 has a reinforced wear plate 73 for applying upper pressure and force on the upper angled hemicylindrical portions 67 and 71 toward each other to cause the first and second lower extending connection tangs 61 & 63 and their connected lower tube hemicylindrical portions 65 and 69 to be urged away from each other.

At the side of the working tube 35 at the transition between the upper angled hemicylindrical portions 67 and 71 and a point just above the first and second lower extending connection tangs 61 & 63 is an external hinge assembly 77. Hinge assembly 77 may include an optional first guide plate 79 and first circular protrusion 81 attached to upper angled hemicylindrical portions 67, and a first slotted plate 83 positioned adjacent to first guide plate 79 and having a slot partially surrounding the circular protrusion 81.

Upper angled hemicylindrical portion 71 has a pair of spaced apart facing surfaces facing a matching pair of facing surfaces of the upper angled hemicylindrical portion 67, of which a dividing line 85 is seen. Upper angled hemicylindrical portions 67 and 71 are be brought together to cause the first and second lower extending connection tangs 61 & 63 and their connected lower tube hemicylindrical portions 65 and 69 to spread apart.

In the View of FIG. 1, the first and second lower extending connection tangs 61 & 63 are shown in a spread apart relationship. A locking pin 87 is seen which can be used to engage angularly spaced apart apertures in the circular protrusion 81 to provide a detent action to hold the working tube 35 in various degrees of spread. Also seen is a slight exterior bevel 89 on the lower tube hemicylindrical portions 65 and 69.

Note the angled separation of the upper angled hemicylindrical portions 67 and 71 and exposing opposing surfaces 91. The angle of the opposing surfaces 91 equals the angle of spread of the first and second lower extending connection tangs 61 & 63.

Referring to FIG. 2, a perspective assembled view illustrates the relative positions of the obturator 33 and working tube 35 in a position for the obturator 33 to be inserted into the working tube 35 and before any spreading takes place.

Referring to FIG. 3, a perspective assembled view illustrates the position of the obturator 33 after it has been inserted into the working tube 35 and again before any spreading takes place. Note that the pivot axes of the first and second lower extending connection tangs 61 & 63 are on par with the pivot axes of the insertion tangs 55. The tip of the obturator 33 extends slightly beyond the bottom most part of the working tube 35 so that the completed assembly can be smoothly urged past muscle and other tissue.

Figure 4:
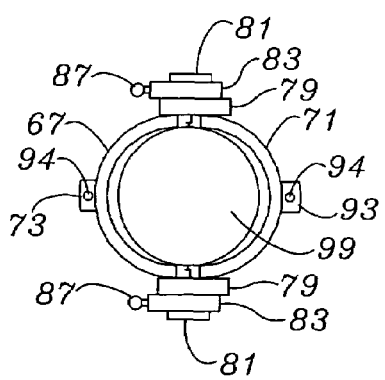
FIG. 4 is a view taken along line 4-4 of FIG. 2 and looking into the working tube of FIG. 1.

Referring to FIG. 4, a view taken along line 4-4 of FIG. 1 is a view looking down into the working tube 35. Other features seen include a wear plate 93 located on the upper angled hemicylindrical portion 71. In both of the wear plates 73 and 93 a universal port 94 is provided as a bore for insertion of a tool or lever to assist in bringing the upper angled hemicylindrical portions 67 and 71 into a tubular relationship. Further, an identical hinge assembly 77 on the side opposite that seen in FIG. 1 is shown with the same numbering as the components which were seen in FIG. 1.

Also seen are a pair of opposing surfaces 95 on upper angled hemicylindrical portion 71 and a pair of opposing surfaces 97 on upper angled hemicylindrical portion 67. Also seen is a central working aperture 99.

Figure 5:
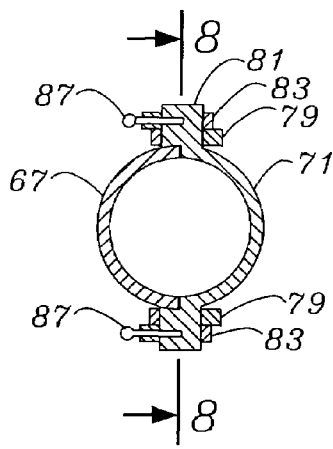
FIG. 5 is a sectional view taken along line 5-5 of FIG. 2 and looking into the hinge of working tube of FIG. 1, illustrating its hinge connections.

Referring to FIG. 5, a view taken along line 5-5 of FIG. 1 is a sectional view looking down into the working tube 35. The connectivity of the structures seen in FIG. 4 are emphasized including the connection of circular protrusion 81 to the upper angled hemicylindrical portion 71, and the connection of first slotted plate 83 to upper angled hemicylindrical portion 67, and which is indicated by the matching section lines Further, an identical hinge assembly 77 on the side opposite that seen in FIG. 1 is shown with the same numbering as the components which were seen in FIG. 1.

Figure 6:
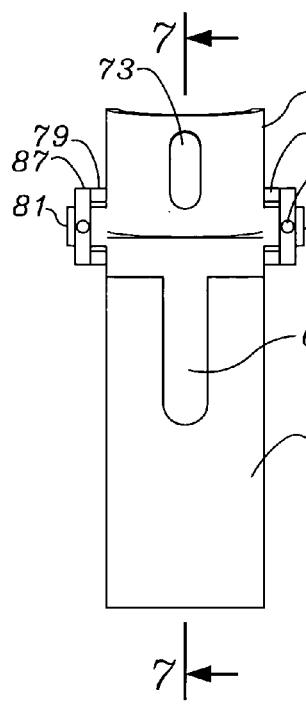
FIG. 6 is an side end view of the working tube of FIGS. 1-5 and illustrating predominantly one of the rigidly connected halves of the invention.

Referring to FIG. 6, a view of one end of the working tube 35 illustrates predominantly the second angled half portion 63. Elements seen in FIGS. 1 and 2 are made more clear in FIG. 3.

Figure 7:
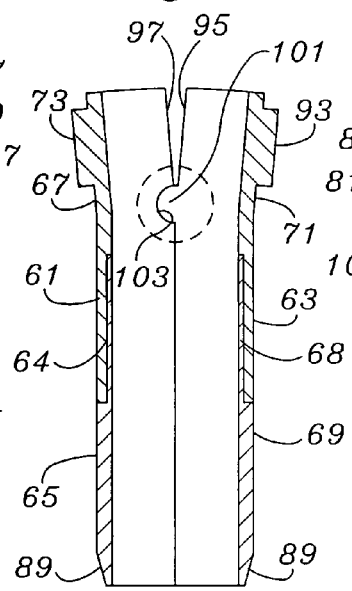
FIG. 7 is a side sectional view taken along line 7-7 of FIG. 6 and showing the internal bearing pivot.

Referring to FIG. 7, a side sectional view taken along line 7-7 of FIG. 6 and shows the internal bearing pivot consisting of a slightly greater than hemispherical side bump projection 101 located on upper angled hemicylindrical portion 71, and a slightly less than hemispherical side circular groove 103 located on upper angled hemicylindrical portion 67. Also seen is the interconnect slots 64 and 68 as well as the first and second lower extending connection tangs 61 and 63. In the showing of FIG. 7 an external bevel 105 is utilized.

Figure 8:
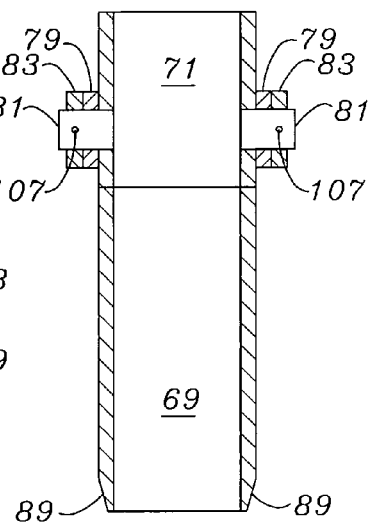
FIG. 8 is a side sectional view taken along line 8-8 of FIG. 5 and illustrating a option for external bevel for the working tube.

Referring to FIG. 8, a side semi-sectional view taken along line 8-8 of FIG. 5 illustrates the integral connectivity of circular protrusion 81 with the upper angled hemicylindrical portion 71. Seen for the first time in isolation are a pair of pin apertures 107 for engaging the locking pin 87.

Figure 9:
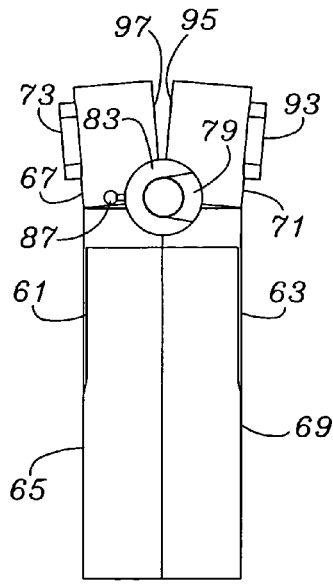
FIG. 9 is a side view of the working tube of FIGS. 1-8 shown with the lower portions in parallel alignment and the upper portions angled with respect to each other.

Referring to FIG. 9, an illustration of a side plan view and in which the lower tube hemicylindrical portions 65 and 69 are in matching straight alignment and forming a lower tube shape, while the upper angled hemicylindrical portions 67 and 71 are angled apart.

Figure 10:
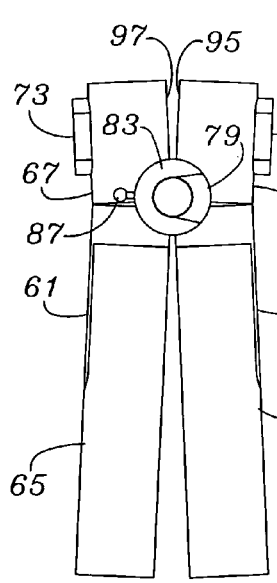
FIG. 10 is a side view of the working tube as seem in FIG. 9 and shown with the lower portions in an angled relationship and the upper portions in a closer angled relationship with respect to each other.

Referring to FIG. 10, a midpoint of movement is illustrates wherein the lower tube hemicylindrical portions 65 and 69 have begun to move apart widening the lower tube shape previously formed into an angled apart opposing hemicylindrical shape, while the upper angled hemicylindrical portions 67 and 71 are brought closer together to have a closer though angled apart an angled apart opposing hemicylindrical shape.

Figure 11:
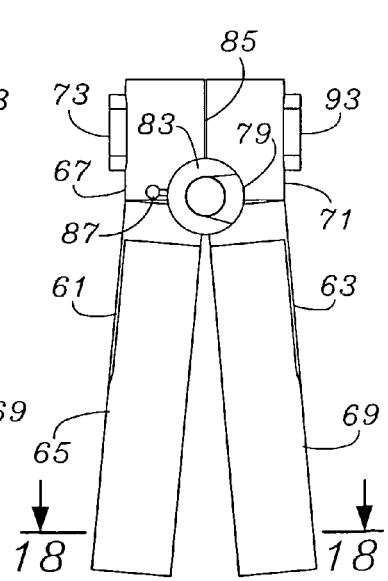
FIG. 11 is a side view of the working tube as seen in FIGS. 9 and 10 and shown with the lower portions in a maximally angled relationship and the upper portions in parallel alignment signaling maximal spread of the lower portions in bringing the upper portions into parallel alignment.

Referring to FIG. 11, a completed movement, with respect to the view of FIG. 4 illustrates a state where the lower tube hemicylindrical portions 65 and 69 have moved apart to their maximum extent into a maximally angled apart opposing hemicylindrical shape, while the upper angled hemicylindrical portions 67 and 71 are brought completely together to form an upper tube shape. It is the position of FIG. 6 which is the ideal working position once the lower tube hemicylindrical portions 65 and 69 are within the body, and provides an expanded working field at the base of the working tube 35. Surgical work is ideally performed through the upper, abbreviated axial length tube shape formed by the upper angled hemicylindrical portions 67 and 71.

Figure 12:
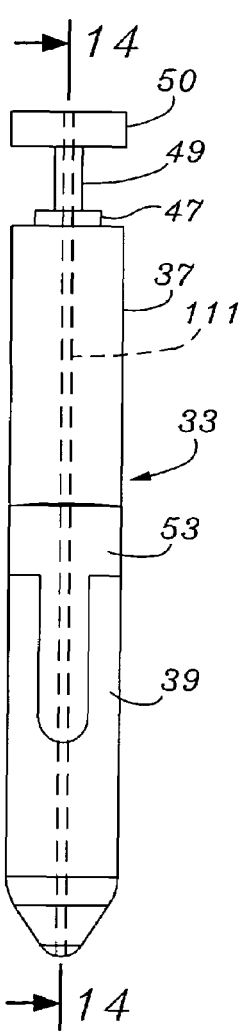
FIG. 12 is a side view of the obturator of FIG. 1 and seen in an assembled view and emphasizing a through bore seen in dashed line format.

Referring to FIG. 12, a side view of the obturator 33 of FIG. 1 is seen in an assembled view and emphasizing in dashed line format a through bore 111 which extends though the obturator 33 from the knurled knob 50 through to the tip of the pair of spreading legs 39 and 41.

Figure 13:
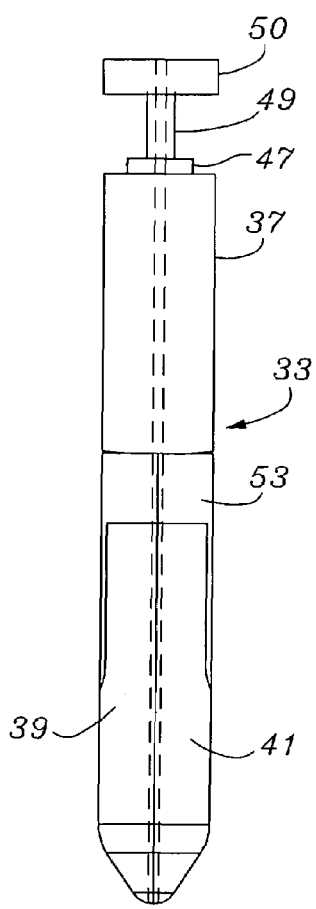
FIG. 13 is a side view of the obturator of FIG. 11 as seen in an assembled view but turned ninety degrees about its axis and emphasizing the through bore.

Referring to FIG. 13, a side view of the obturator 33 of FIG. 11 is seen in an assembled view but turned ninety degrees about its axis, and agin emphasizing in dashed line format the through bore 111 which extends though the obturator 33 from the knurled knob 50 through to the tip of the pair of spreading legs 39 and 41. It is from this position that further actuation will be illustrated.

Figure 14:
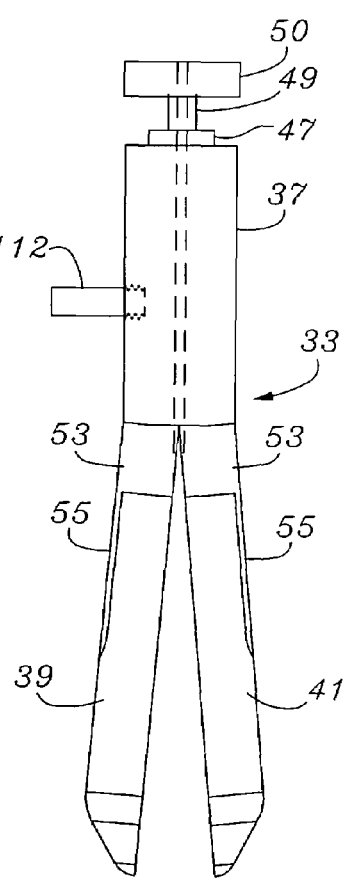
FIG. 14 shows a side view of the obturator 33 of FIG. 13 with the spreading legs in an angled apart relationship.

Referring to FIG. 14, a side view of the obturator 33 of FIG. 13 is seen but with the spreading legs 39 and 41 in an angled apart relationship. An optional support 112 is supported by the upper control housing 37 to enable independent support and locationing of the obturator 33 should it be needed. Once the knurled knob 50 is turned, the wedge 51 seen in FIG. 1 is driven downward causing the spreading of the spreading legs 39 and 41.

Referring to FIG. 15, a sectional view taken along line 14-14 of FIG. 12 gives a sectional view from the same perspective seen in FIG. 14. Pivot blocks 59 are seen as having pivot bores 113 which enable the upper portions 53 to pivot with respect to the upper control housing 37 and which enable the downward movement of the wedge 51 to translate into a spreading of the spreading legs 39 and 41.

As can be seen, the knob 50 and control shaft 49 and the wedge 51 have the through bore 111. In the configuration shown, the control shaft 49 includes a threaded portion 113 which engaged an internally threaded portion 115 of an internal bore 117 of the upper control housing 37. The boss 47 is shown to be part of a larger insert fitting within a larger fitted bore 119 within the upper control housing 37. This configuration pushes the wedge 51 downwardly against an internal wedge conforming space 123 to cause the insertion tangs 55 and upper portions 53 to spread apart. The wedge conforming space 123 need not be completely wedge shaped itself, but should ideally have a surface which continuously and evenly in terms of area engages the wedge 51 to give even control. Further, the wedge 51 can be configured to be rotatable with or independently rotationally stable with respect to the control shaft 49. As can be seen, the through bore 111 continues below the internal wedge conforming space 123 as a pair of hemicylindrical surfaces 125 in the upper portion 53, as well as a pair of hemicylindrical surfaces 127 in the pair of spreading legs 39 and 41.

Referring to FIG. 16 a view of obturator 33 similar to that of FIG. 15, but turned ninety degrees along its axis is seen. In this view, the wedge 51 is seen as having a narrower dimension to lend internal stability by narrowing the bearing area of the wedge 51 action in opening the pair of spreading legs 39 and 41.

Referring to FIG. 17, a closeup view of the external hinge assembly 77 seen in FIG. 1 illustrates the optional use of a plug 131 to cover the exposed side of the circular protrusion 81.

Referring to FIG. 18, a view taken along line 18-18 of FIG. 11 illustrates a view which facilitates the showing of an optional skirt, including a skirt section 133 welded or otherwise attached to lower tube hemicylindrical portion 65, and a skirt section 133 welded or otherwise attached to lower tube hemicylindrical portion 69. The skirts sections 133 and 135 are made of thin flexible metal and interfit within a pair of accommodation slots 137 and 139, respectively.

Figure 19:
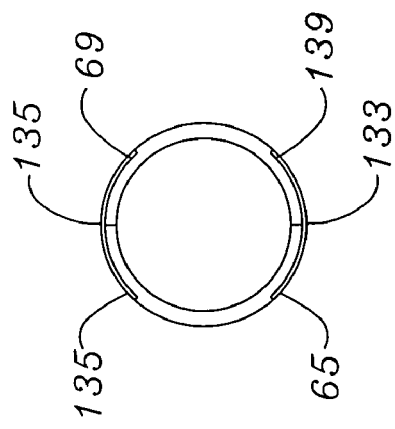
FIG. 19 is a view of the lower tube hemicylindrical portions 65 and 69 in a close relationship illustrating the manner in which the skirts sections within their accommodation slots areas.

Referring to FIG. 19, a view of the lower tube hemicylindrical portions 65 and 69 in a close relationship illustrates the manner in which the skirts sections 133 and 135 fit within the accommodation slots 137 and 139 when the lower tube hemicylindrical portions 65 and 69 are brought together to a circular configuration.

Figure 20:
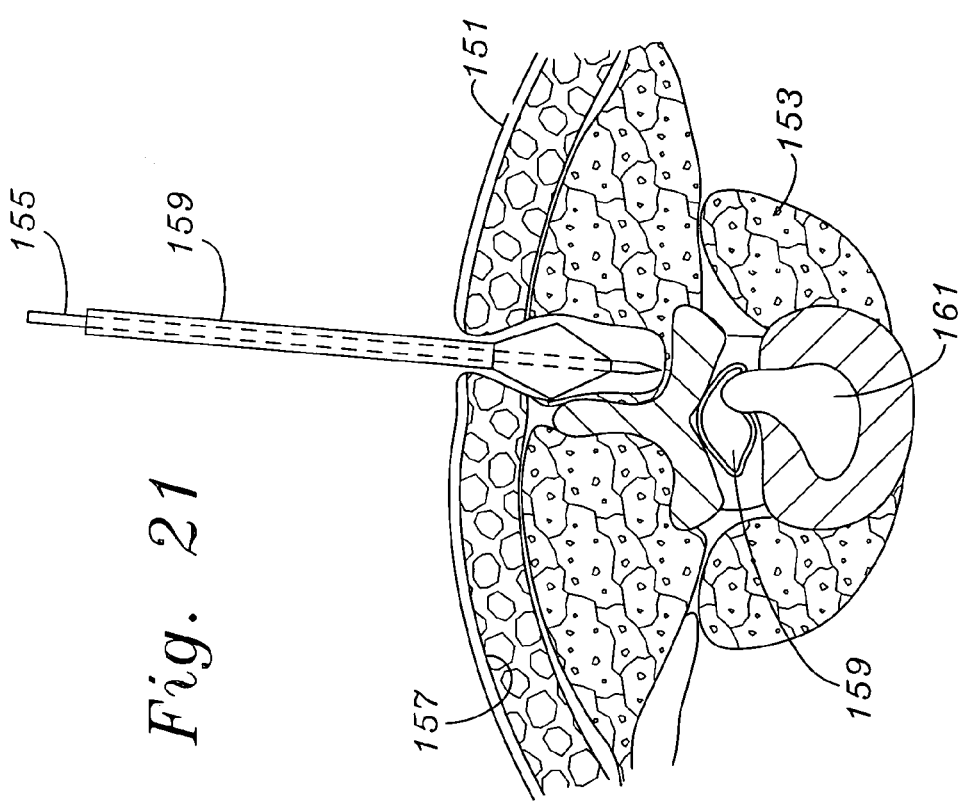
FIG. 20 is a cross sectional view of the a patient and spine and facilitates illustration of the general sequence of steps taken for many procedures utilizing the minimal incision maximal access system disclosed.

Referring to FIG. 20, a cross sectional view of the a patient 151 spine 153 is shown for illustration of the general sequence of steps taken for any procedure utilizing the minimal incision maximal access system 31. There are several procedures utilizable with the minimal incision maximal access system 31. Only a first procedure will be discussed using illustrative figures. Other procedures will be discussed after minor variations on the minimal incision maximal access system 31 are given below.

Procedure I: Diskectomy and Nerve Decompression

The patient 151 is placed prone on radiolucent operating table such as a Jackson Table. The patient 151 is then prepared and draped. The operative area is prepared and localized and an imaging device is prepared. A guide pin 155 is insert through the patient's skin 157, preferably under fluoroscopic guidance. In the alternative and or in combination, the patient 151 skin can be incised with a scalpel. Other features in FIG. 20 include the dural sac 159, and ruptured intervertebral disc 161.

Figure 21:
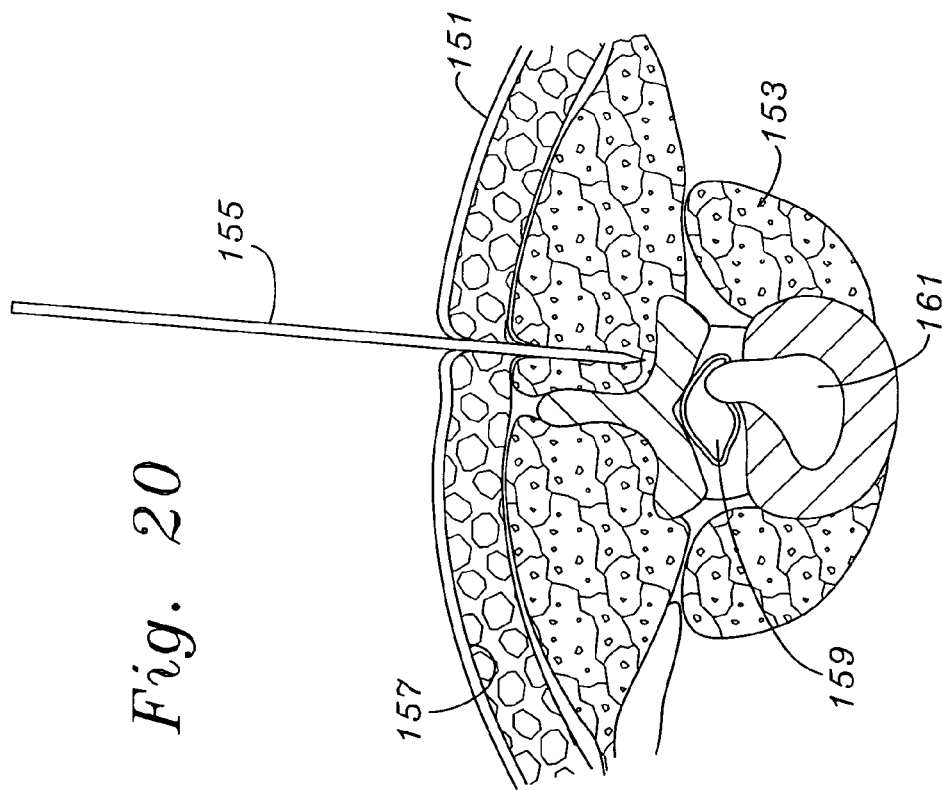
FIG. 21 illustrates a fascial incisor overfitting a guide pin and further inserted to cut through external and internal tissue.

Referring to FIG. 21, a fascial incisor 169 overfits the guide pin 155 and is further inserted to cut through external and internal tissue. The fascial incisor 169 is then removed while the guide pin 155 is left in place. Next, using the obturator 33, the surgeon clears the multifidus attachment with wig-wag motion of the obturator 33 tip end. Next the obturator 33 is actuated to gently spread the multifidus muscle, and then closed.

Figure 22:
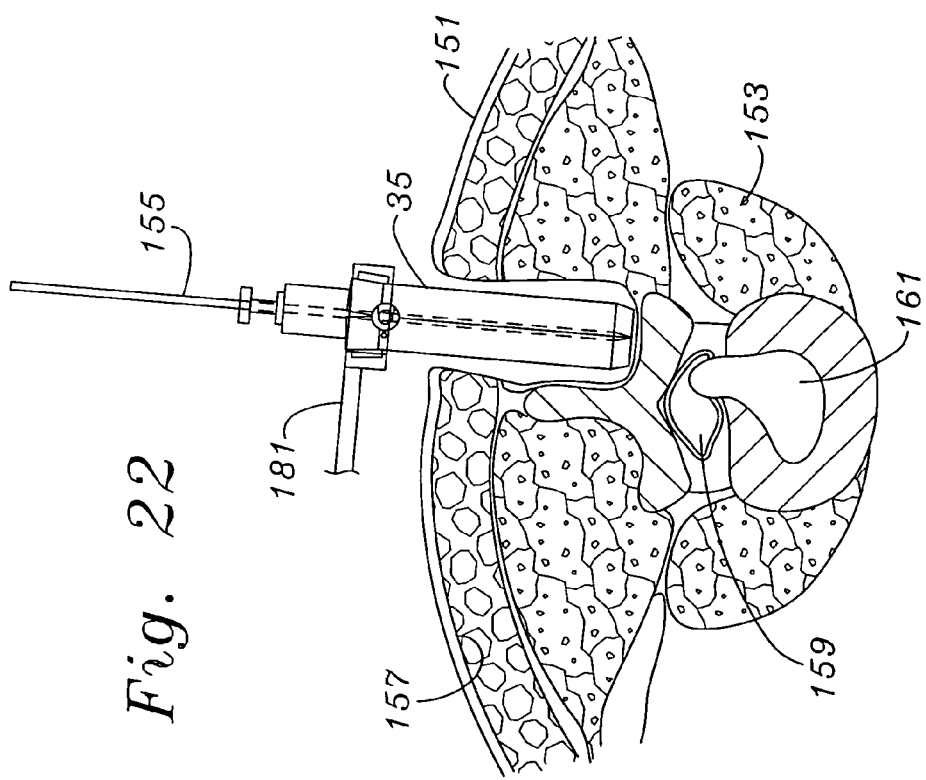
FIG. 22 illustrates the assembled Working Tube—Obturator being inserted into the area previously occupied by the fascial incisor and advanced to the operative level lamina.

Referring to FIG. 22, next the assembled Working Tube 35—Obturator 33 is inserted into the area previously occupied by the fascial incisor 169 and advanced to the operative level lamina and remove the obturator 33. As an alternative, and upon having difficulty, the obturator 33 could be initially inserted, followed by an overfit of the working tube 35. In another possibility, a smaller size of obturator 33 and working tube 35 or combination thereof could be initially utilized, followed by larger sizes of the same obturator 33 and working tube 35. The assembled Working Tube 35—Obturator 33 in place is shown in FIG. 22 with the working ends very near the spine.

Figure 23:
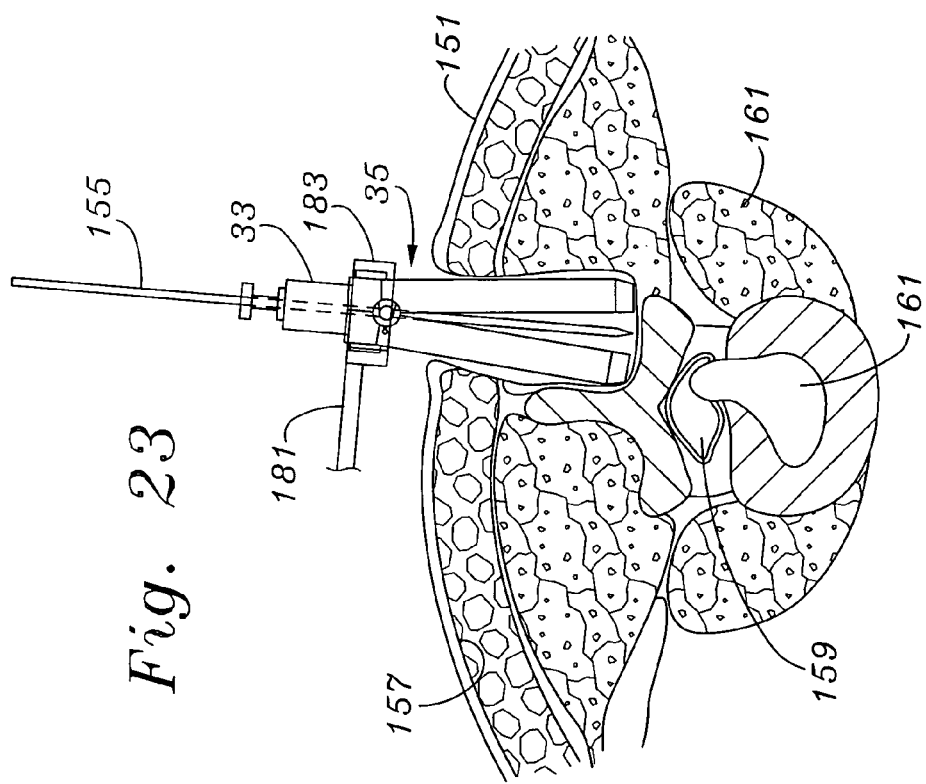
FIG. 23 illustrates the obturator 33 being actuated to a spread orientation to which automatically actuates the working tube to a spread orientation.

Referring to FIG. 23, the obturator 33 is actuated to a spread orientation, which automatically actuates the working tube 35 to a spread orientation. Spread is had to the desired exposure size. The obturator 33 is thin actuated to a closed or non-spreading position. The obturator and working tube is then again advanced to dock on the spine. The working tube 35 is then fixed to assume an open position either by utilization of the locking pin 87 or other fixation device to cause the working tube 35 to remain open. Then, once the working tube 35 is locked into an open position, the obturator 33 is actuated to a closed or non-spread position and gently removed from the working tube 35.

Figure 24:
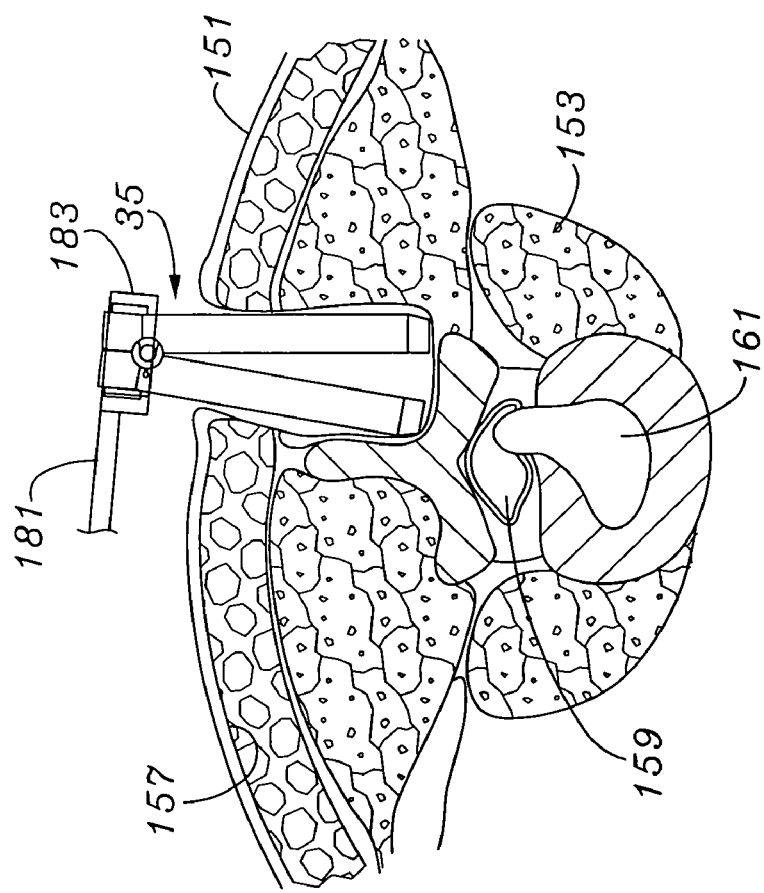
FIG. 24 is a view of the working tube 35 is in place and supported, held or stabilized in the field of view by a telescopy support arm and engagement, the opposite end of the stabilizing structure attached to the operating table.

Referring to FIG. 24, the working tube 35 is in place. The working tube 35 may be secured by structure ultimately attached to an operating table. The working tube 35 may be held or stabilized in the field of view by a support 181 which may have an engagement sleeve 183 which fits onto the working tube. As can be seen, the operative field adjacent the spine area is expended even though the incision area is limited. The deeper a given size of working tube 35 is inserted, the smaller its entrance area. After the working tube 35 is stabilized, the surgeon will typically clear the remaining multifidus remnant at the working level and then set up and insert an endoscope or use operating microscope or loupes. The surgeon is now ready to proceed with laminotomy.

Figure 25:
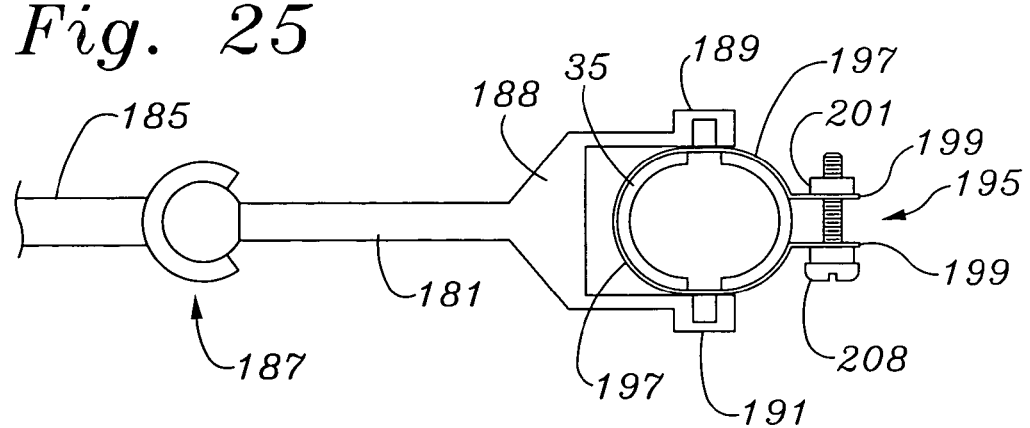
FIG. 25 illustrates further details of the support arm seen in FIG. 24, especially the use of a ball joint.

Referring to FIG. 25, further detail on the support 181 and engagement sleeve 183 is shown. A base support 185 may support a ball joint 187, which may in turn support the support 181. The support 181 is shown as supporting a variation on the engagement sleeve 183 as a pivot point support engagement end 188 having arm supports 189 and 191. The arm supports 189 and 191 engage the external pivot structure on the working tube 35 which was shown, for example, in FIG. 1 to be the external hinge assembly 77.

As a further possibility, the upper angled hemicylindrical portions 67 and 71 are shown as being engaged about their outer periphery by an adjustable clamp 195. Adjustable clamp 195 includes a band 197 encircling the upper angled hemicylindrical portions 67 and 71. The ends of band 197 form a pair of opposing plates 199 and are engaged by a nut 201 and bolt 203 assembly.

Figure 26:
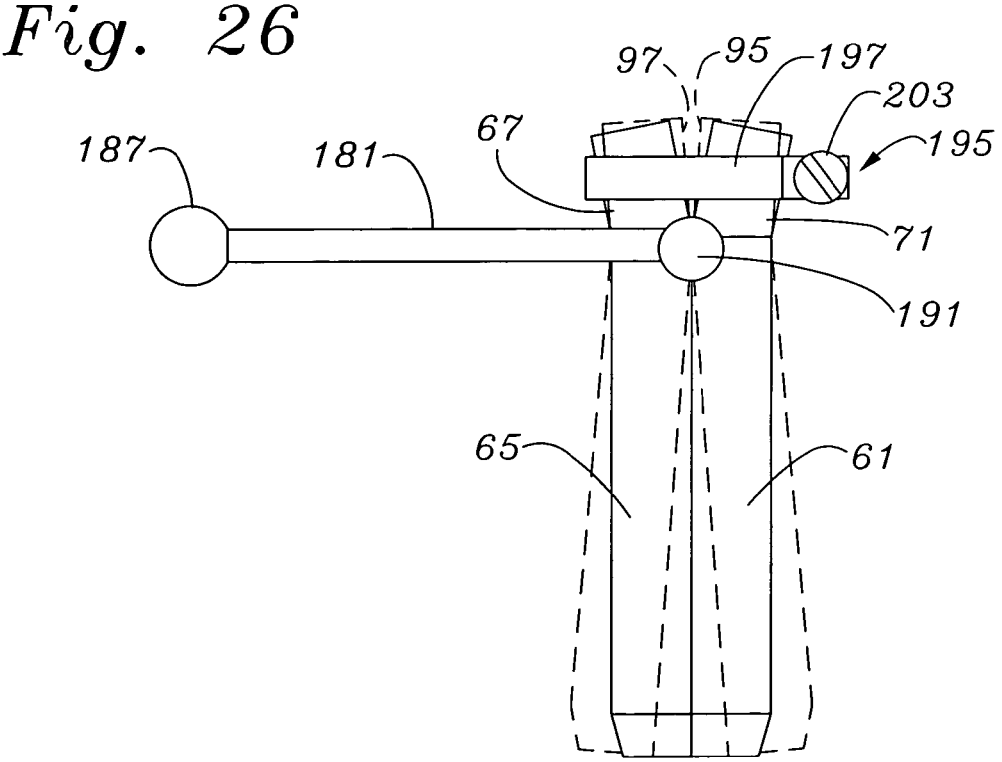
FIG. 26 illustrates a side view of the assembly seen in FIG. 25 is seen with an adjustable clamp operable to hold the working tube open at any position.
Figure 27:
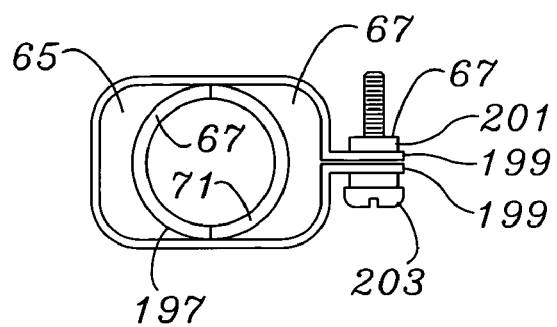
FIG. 27 is a top view looking down upon the adjustable clamp seen in FIGS. 25-26 and shows the orientation of the working tube and adjustable clamp in fully closed position.

Referring to FIG. 26, a side view of the assembly seen in FIG. 25 is seen with the adjustable clamp 195 operable to hold the working tube 35 open at any position. Referring to FIG. 27, a top view looking down upon the adjustable clamp 195 seen in FIGS. 25-27 shows the orientation of the working tube 35 and adjustable clamp 195 in fully closed position. When used in conjunction with the adjustable clamp 195, the Reinforced wear plates 73 and 93 are eliminated so as to provide a smooth interface against the exterior of the upper angled hemicylindrical portions 67 and 71.

Figure 28:
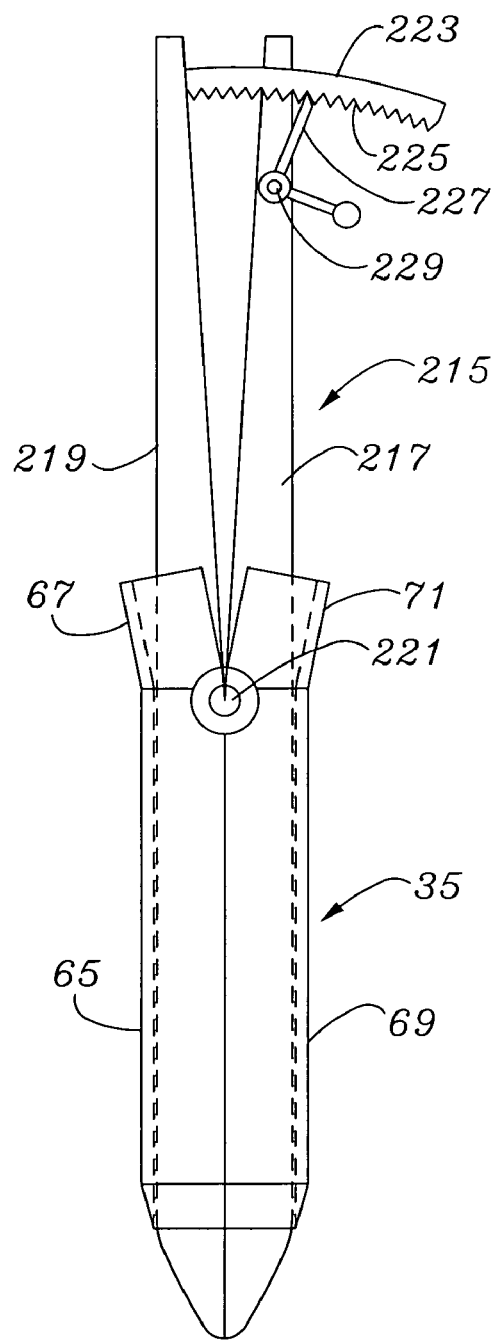
FIG. 28 shows a variation on the obturator seen previously in FIG. 1 and illustrates the use of handles which are brought together.

Referring to FIG. 28, a variation on the obturator 33 is seen. An obturator 215 has handles 217 and 219 which operate about a pivot point 221. A working tube 222 is somewhat simplified but is equivalent to the working tube 35 and is shown as including upper angled hemicylindrical portions 67 and 71. Handle 219 has a ratchet member 223 extending from it and a latch 227 pivotally connected about pivot point 229 to handle 217.

Figure 29:
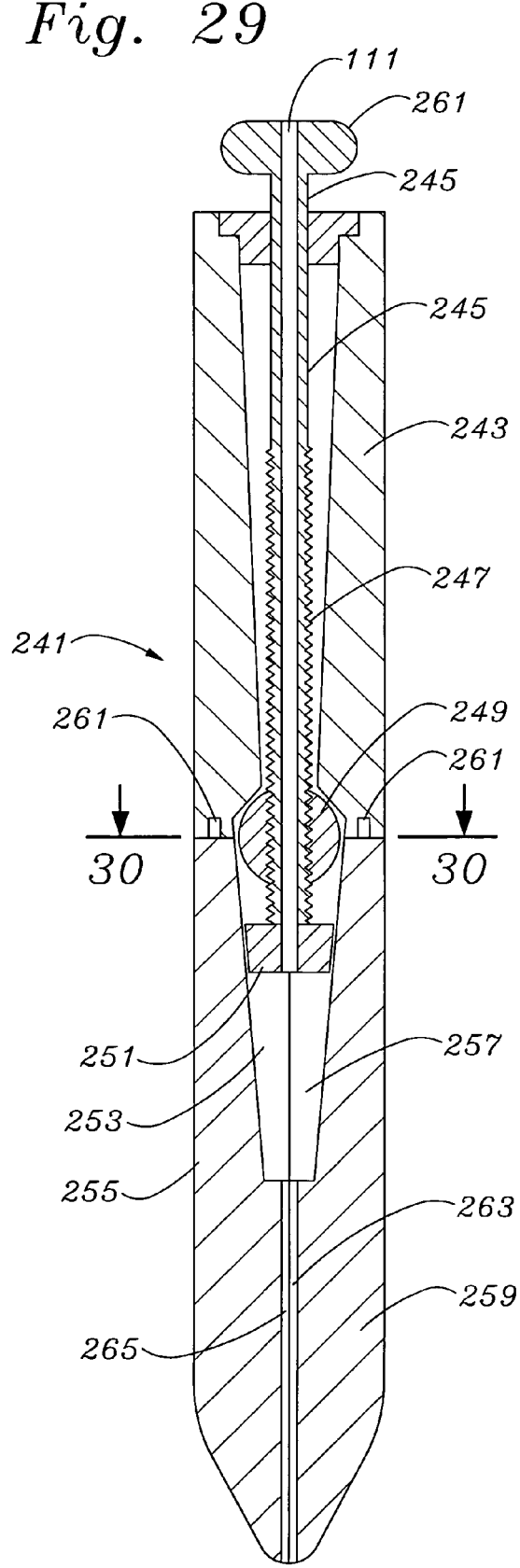
FIG. 29 illustrates a further variation on the obturator seen previously in FIG. 1 and illustrates the use of a central ball nut.

Referring to FIG. 29, a variation on obturator 33 is seen as an obturator 241 having an upper housing 243, control shaft 245 having a threaded section 247 and operating through a ball nut 249. A wedge 251 is extendable down through an operation space made up of a half space 253 in a leg 255 and a half space 257 in a leg 259. Hinge structures 261 are shown attaching the legs 255 and 259 to the upper housing 243. A through bore 111 is also seen as extending from the knob 261 through to the bottom of the wedge 251. An access groove 263 is carried by the leg 259 while An access groove 263 is carried by the leg 259 while an access groove 265 is carried by the leg 255.

Figure 30:
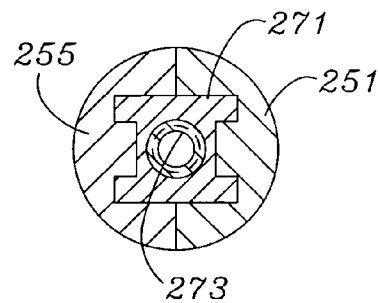
FIG. 30 is a sectional view taken along line 30-30 of FIG. 29 and illustrates the use of a central support block to support the central threaded surface.

Referring to FIG. 30, a sectional view taken along line 30-30 of FIG. 29 illustrates the use of a central support block 271 to support the a central threaded surface 273 and the legs 255 and 259.

Figure 31:
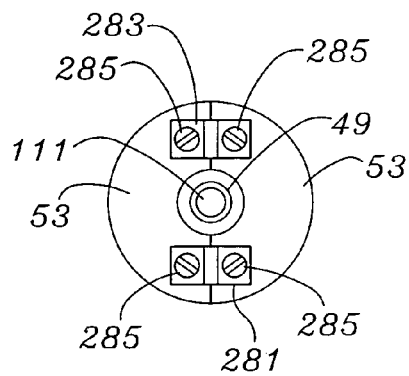
FIG. 31 is a top view of a thin, inset hinge utilizable with any of the obturators herein, but particularly obturators of FIGS. 1 and 29.

Referring to FIG. 31, a view of a thin, inset hinge 281 utilizable with any of the obturators, but particularly obturators 33 and 241, is shown. In the case of obturator 33, by way of example, upper portions 53 accommodate control shaft 49 with its through bore 111. Inset hinge 281 may be implaced with an inset 283 and secured with machine screws 285. Inset hinge 281 may be made of a "living hinge" material such as a hard plastic, or it can have its operations base upon control bending of a pre-specified length of steel, since the angle of bend is slight. The connection between the upper portions 53 and the upper control housing 37 may be by any sort of interlocking mechanism, the aforementioned pivot blocks 59 or other mechanism.

Referring to FIG. 32, a sectional view of the obturator 33 within the working tube 35 is seen. The wedge 51 is seen at the bottom of the internal wedge conforming space 123. Once the spreading of the working tube 35 is accomplished the working tube 35 is kept open by any of the methods disclosed herein. Also seen is a pivot ball 116 to allow the control shaft 49 to turn with respect to the wedge. The pivot ball will continue to support a central aperture bore 111. Once the working tube 35 is stabilized in its open position, the obturator 33 is returned to its collapsed state as is shown in FIG. 33.

Figure 34:
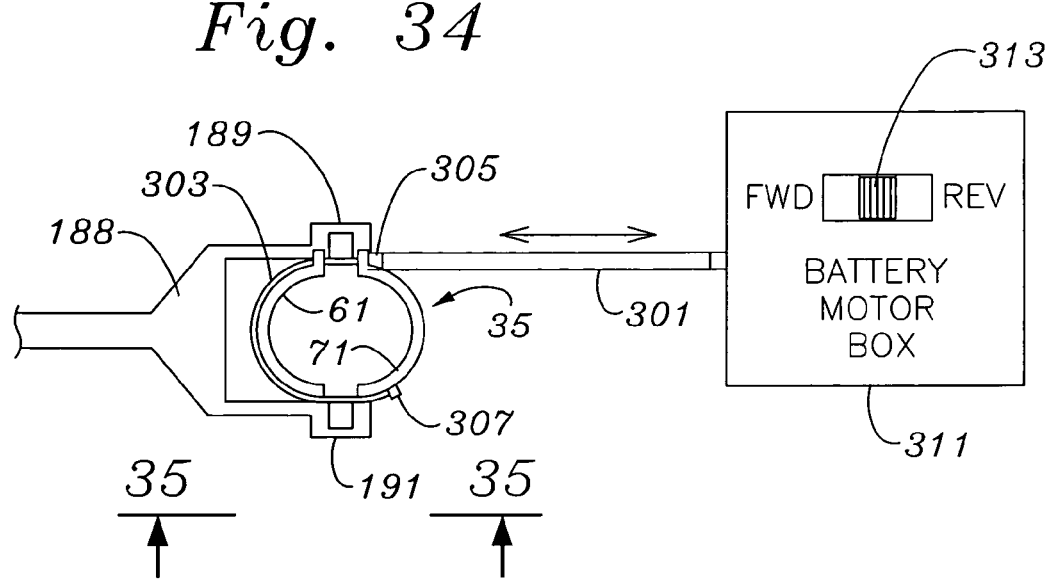
FIG. 34 illustrates a top and schematic view of the use of a remote power control to provide instant control of the working tube using an adjustable restriction on the upper angled hemicylindrical portions of the working tube.

Provision of electromechanical power to the operation of the working tube 35 can provide a surgeon an additional degree of instant control. Referring to FIG. 34, a top and schematic view of the use of a remote power control to provide instant control of the working tube 25, similar to the view seen in FIG. 25 illustrates the use of a remote annular control cable 301 using an internal cable 303 which is closely attached using a guide 305 and which circles the upper angled hemicylindrical portion 67 and 71, terminating at an end fitting 307.

The annular cable 301 is controlled by a BATTERY MOTOR BOX 311 having a forward and reverse switch 313 (with off or non actuation being the middle position). This enables the surgeon to expand the surgical field as needed and to collapse the surgical field to focus on certain working areas. BATTERY MOTOR BOX 311 is configured with gears to cause the cable 303 to forcibly move axially within the annular cable 301 to transmit mechanical power to the working tube 35.

Figure 35:
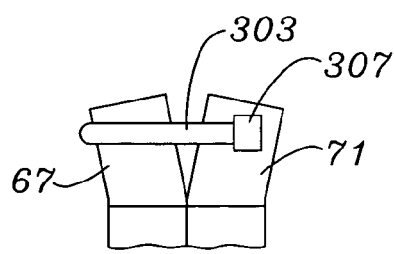
FIG. 35 is a view taken along line 35-35 of FIG. 34 and illustrating the method of attachment of the cable or band constriction.

Referring to FIG. 35, a view taken along line 35-35 of FIG. 34 illustrates how the cable 303 is held in place and a closeup of the end termination 307.

Figure 36:
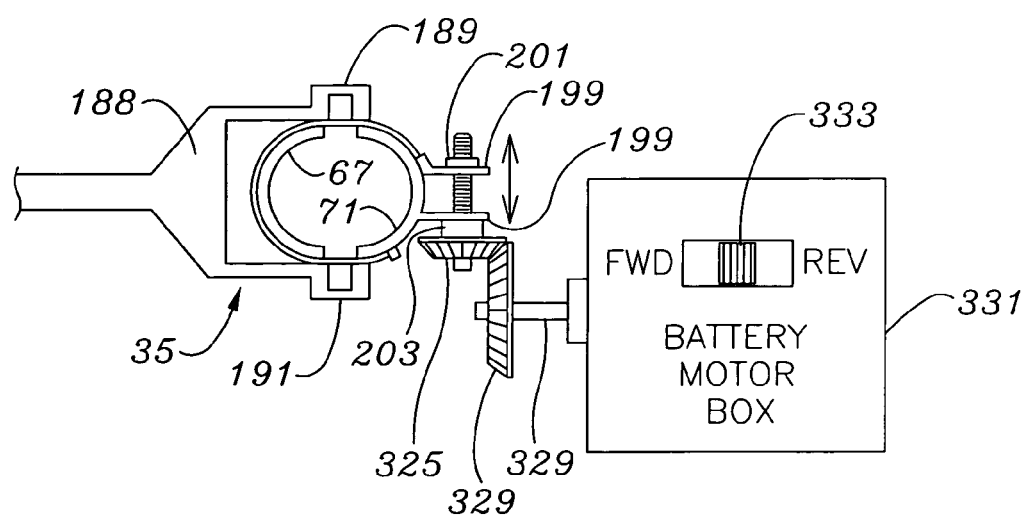
FIG. 36 is a mechanically operated version of the nut and bolt constriction band seen in FIG. 25.

Referring to FIG. 36, a mechanically operated version of the nut 201 and bolt 203 constriction band seen in FIG. 25. The mechanical power linkage can be provided remotely as by a rotating annular cable, but the basic mechanical setup shown illustrates the mechanical principles. On the bolt 203, a gear head 325 is implaced, either by attachment or by the provision of a threaded member and gear head made together. A second gear head 327 is utilized to show the possibility of providing a right angle power take-off in the event that the power connection interferes with the area around the surgical field. A shaft 329 extends from a BATTERY MOTOR BOX 331. The BATTERY MOTOR BOX 331 has a forward and reverse switch 333, (with off or non actuation being the middle position). Shaft 329 could be flexible and connected directly into axial alignment with the threaded member of bolt 201 or an integrally formed threaded member.

Advantages Over Existing Surgical Techniques

In terms of general advantages, there are differences between the minimal incision maximal access system 31, and its components as described in all of the drawings herein (but which will be referred throughout herein simply as the minimal incision maximal access system 31, or simply system 31) and other devices and procedures.

1. With regard to the Traditional microdiskectomy technique, the minimal incision maximal access system 31 allows for at least the same, if not better visualization access of the operative field. System 31 offers the same 3-Dimensional work ability or, if preferred, an endoscope can be utilized. System 31 minimizes muscle injury with spread versus extensive cautery dissection. System 31 has clear advantage on the challenging obese and very large patient where the traditional microdiskectomy technique is almost impossible to be applied.

2. With regard to open pedicle screw insertion procedures, system 31 offers muscle approach minimizing muscle devascularization and denervation. The traditional approach had required at least one level proximal and one level distal additional exposure causing extensive muscle injury often leading to "fibrotic" muscle changes resulting in chronic painful and stiff lower back syndrome. System 31 offers the most direct approach to the pedicle entry point selecting the avascular plane between the longissimus and multifidus muscles.

3. With regard to the Sextant Procedure, system 31 offers clear advantage over the Sextant procedure. First, the system 31 offers a procedure which is not a blind pedicle screw technique. System 31 can be applied to larger and more obese patients in which the Sextant procedure cannot be utilized. In this procedure using system 31 oosterolateral fusion can be performed along with insertion of the pedicle screws. The sextant procedure is strictly a tension band stabilization.

In general, the components of the minimal incision maximal access system 31 are very simple the hemispherical shapes used for the working tube can be round or oval. A keying system can be had to align the obturator 33 to the working tube 35. In the case of an oval system, the alignment would be automatic.

The minimal incision maximal access system 31 is a modular system with interchangeable parts for both the working tube 35 and the obturator 33. The guide Pin 155 is of simple construction, as is the fascial incisor 169. The working tube 35 has a limited number of basic parts, and can be made in the simple, two main piece version of FIG. 28, or the multi-piece version of FIG. 1, which enables retractor-sleeve substitution. A hinge and stabilization mechanism completes the simplified construction.

The obturator 33 is also of simple construction, with upper control housing 37, pair of spreading legs 39 and 41, and an internal hinge, whether the pivot blocks 59 or hinge 281 and its ability to support a control shaft 49 having a bore 111 for a guide pin 155. Guide pin 155 may preferably have a size of from about 0.3 mm to 0.40 mm diameter and 30 cm to 40 cm in length. The fascial incisor may preferably be cannulated for usage with the guide pin 155 and have a width of about 2 mm more than the associated retractor. The overall cutting head length of about 1.2 cm has a shape as indicated in the Figures and has a thickness slightly larger than that of the guide pin 155.

The working tube 35 can have several variations and added details including the simplest shapes as dictated by intended usage. Working tube 35 can have a simple fluted hemitube shape or a Slanted box shape. Further, the possibility of a fluted oval shape is dictated when the approach is more angular. The working tube 35 can have an attachment for an endoscope. Working tube 35 can also have a non-symmetric appearance as by having longitudinal cross sectional shape with half of its shape being rounded and one half of its shape being rectangular or box shaped. This could also give rise to a similarly shaped obturator 33. The working tube 35 should have an anti-reflective inner coating and may be of modular construction.

The preferred lower dimensions for the lower tube hemicylindrical portions 65 and 69 include an overall shape which is semi tubular round or oval and having a width of from about 1.6-3.0 cm and a length of from about 4.0-18 cm. Hemicylindrical portions 65 and 69 may have custom cut outs depending upon planned application.

The hinge assembly 77 may have male-female post or male-female dial lock design, as well as a hinge housing and a bias (by spring or other mechanism) to keep angular displaceable portions of the working tube 35 closed. A "universal" port provides a point of attachment of an endoscopic or stabilizer bar.

The obturator 33 may be any controlled opening device including a circular band or cable, force Plates, or a device attached to hinge assembly 77 or other hinge assembly.

All sleeve attachments including the attachable legs 39 and 41, as well as the lower tube hemicylindrical portions 65 and 69 should be of the friction grip type or snap and lock type or other suitable connection method or structure.

Obturator 215 may have squeeze grip scissor style handles 219 and 217 and a controlled dilator. It may utilize an enclosed design with a handle cover having a no-slip surface. It may be attached to the hinge housing of the working tube or separate hinge housing. In fact, it may be of a design to be held in place solely by the working tube 35. Ideally a cavity will be provided through the center axis to contain the shaft for the dilator mechanism if applicable.

The central bore 111 of the obturator 33 may have a diameter of from about 5-10 mm, depending upon the size of the obturator 33 utilized. Obturator 33 should be provided in various widths and length to match working tube. The working tips of the spreading legs 39 and 41 may be changeable according to surgical procedures as described in the operative procedures herein. It may have an inner chamber, or internal wedge conforming space 123 slanted in shape wider proximal and more narrow distal to accommodate the wedge 51. The internal wedge conforming space 123 can be enclosed with expanding, contracting sleeve.

Other Procedures

Many other procedures can be facilitated with the use of the inventive minimal incision maximal access system 31 and methods practiced therewith. Procedure I, a diskectomy and nerve decompression procedure was described above with reference to the Figures. Other procedures are as follows:

Procedure II: Facet Fusion

1. Patient prone on Jackson Table with normal lordosis preserved. This can be increased by placing additional thigh and chest support to increase lumbar lordosis.
2. Insert percutaneous special guide pin perpendicular to the floor at a point 1 cm caudal to the Alar-Superior facet notch.
3. Apply a flag guide to a first guide pin 155 #1.
4. Measure skin to bone depth from the scale on guide pin 155 #1.
5. Slide drill guide mechanism on the flag guide to match the skin bone distance.
6. Insert guide pin 155 #2 through the drill guide to dock on the superior facet.
7. Make a small skin incision for the obturator 33.
8. Working tube 35 should be small oval or round with medial cutout to maximally medialize the working tube 35.
9. Advance the working tube 35 to the L5-S1 joint and dock.
10. Drill the guide pin across the joint medial to lateral, rostral to caudal. If in proper position, advance across the joint to engage the ala.
11. Drill across the joint with a cannulated drill.
12. Check depth flouroscopically and measure.
13. Pick appropriate screw length.
14. Insert specially designed facet screw and protective bracket, secure tightly.

Procedure III: Posterior Lumbar Interbody Fusion (PLIF)

1. First half of the procedure similar to microdiskectomy (Procedure I) except for the use of a larger diameter sized working tube 35. Use a 20-25 mm round or elliptical diameter working tube 35 with a medial cutout to allow docking as close to midline as possible.
2. Following diskectomy enlarge the laminotomy to accommodate the tools use for the specific PLIF such as Brantigan cage or Tangent.

Procedure IV: Transfacet Interbody Fusion (TFIF)

1. Follow the same procedure as the PLIF in terms of selecting and inserting the Working Tube 35.
2. Following the diskectomy, resect the facet joint.
3. Approach the posterolateral disc space through the medial ⅔ of the facet joint. Take care not to injure the exiting root above.
4. Proceed with Brantigan cage instruments and interbody cages.

Procedure V: Pedicle Screw Instrumentation Technique

1. Place the patient 151 Prone position on a Jackson Table.
2. Guide pin 155 is docked on facet joint angled 30 degree lateral to medial in the plane between the longissimus muscle longitudinally and multifidus muscle medially.
3. Make skin incision.
4. Fascial incisor introduction.
5. Introduce the obturator 33 working tube 35 assembly between the longissimus and multifidus and progressively open the obturator 33 tip ends of the legs 39 and 41*p*, gradually reaching from the joint above and the joint below.
6. Advance the working tube 35 and retract the obturator 33.
7. Use the elliptical Working Tube size 2.5 cm wide and open up to 5 cm.

Procedure IV: Anterior Lateral Lumbar Diskectomy Fusion

1. Mid lateral decubitus position left side up. Place a "waist roll" to prevent sag of the mid lumbar spine.
2. Identify proper level of surgery fluoroscopically.
3. Insert a guide pin 155 #1 percutaneously into the superior facet perpendicular to the spine.
4. Measure depth skin to joint on the scaled guide pin 155 #1.
5. Insert cannulated flag guide over guide pin 155 #1.
6. Slide the drill guide to match the depth.
7. Insert a guide pin 155 #2 down to the disc space.
8. Make skin incision and insert fascial cover.
9. Insert the working tube 35 and Obturator 33 combination.
10. Progressively dilate the obturator 33.
11. Advance the working tube 35.
12. Perform anterolateral diskectomy and interbody fusion as taught above.
13. Use a round or oval shaped retractor or lower tube hemicylindrical portion 65 and 69 as inserts preferably with distal end cutouts in each.

Procedure VII: Posterior Cervical Foramenotomy and Lateral Mass Plating

1. The patient is placed in a prone position on a Jackson table.
2. Fluoroscopic identification of the level of surgery is had.
3. Percutaneously insert guide pin 155 with AP and lateral fluoroscopic views.
4. Make the initial skin incision.
5. Apply the working tube 35 with obturator 33 into the incision.
6. Perform slow dilation of the muscle.
7. Advance the working tube 35 and collapse and remove the obturator 33.
8. Proceed with surgery. Type of sleeve or lower tube hemicylindrical portion 65 should be round or oval with slanted and to match the slanted lamina.
9. For application for Lateral mass plating use an oval working tube 35 for a greater exposure.

Procedure VIII: Anterior Cervical Diskectomy Fusion

1. Begin with standard anterior cervical diskectomy fusion approach with a incision on the left or right side of the neck.
2. Blunt finger dissection is performed between the lateral vascular structures and the medial strap muscle and visceral structures down to the prevertebral fascia.
3. Establish the correct level to be operated on fluoroscopically and the guide pin 155 inserted into the disc.
4. Apply the working tube 35 and obturator 33 combination and dock at the proper level of the anterior sping.
5. Open the working tube 35 and obturator 33.
6. Mobilize longus colli muscle.
7. Use special Bent Homen Retractor specifically design to retract the longus colli.
8. Proceed with surgery.

Procedure IX: Anterior Lumbar Interbody Fusion

1. Begin with the standard approach whether it is retroperitoneal, transperitoneal or laparoscopic.
2. Apply the special anterior lumbar interbody fusion working tube 35 and obturator 33. This is a design with a medial lateral opening. It is oval shape and preferably with skirts 133 and 135. The distal end of the retractor sleeve is slightly flared outward to retract the vessels safely. There is a skirt 133 or 135 applied to the cephalad side and possibly to the caudal side.
3. With the vessels and the abdominal contents safely retracted out of harms way, proceed with diskectomy and fusion.

While the present system 31 has been described in terms of a system of instruments and procedures for facilitating the performance of a microscopic lumbar diskectomy procedure, one skilled in the art will realize that the structure and techniques of the present system 31 can be applied to many appliances including any appliance which utilizes the embodiments of the instrumentation of the system 31 or any process which utilizes the steps of the system 31.

Although the system 31 has been derived with reference to particular illustrative embodiments thereof, many changes and modifications of the system 31 may become apparent to those skilled in the art without departing from the spirit and scope of the system 31. Therefore, included within the patent warranted hereon are all such changes and modifications as may reasonably and properly be included within the scope of this contribution to the art.

What is claimed is:

1. An obturator comprising:
   an upper control housing having a bore therethrough, at least a portion of said bore having an internal threaded surface;
   a control shaft extending through said upper control housing bore having a first end and a second end and having an externally threaded surface complementary and engaging said internal threaded surface of said bore of said upper control housing;
   a wedging member attached at said second end of said control shaft;
   a first spreading leg pivotally mounted with respect to said upper control housing and carrying at least a first portion of an internal wedge conforming space surrounding said wedging member;
   a second spreading leg pivotally mounted with respect to said upper control housing and carrying at least a second portion of said internal wedge conforming space surrounding said wedging member, whereby movement of said wedging member causes said first and said second spreading leg to move angularly away from each other upon the turning of said control shaft.

2. The obturator of claim 1 wherein said first and second spreading legs are hingeably attached to said control housing.

3. The obturator of claim 1 wherein said first and second spreading legs are hingeably attached to each other.

4. The obturator of claim 1 and further comprising a central support block attached to said first and second spreading legs.

5. The obturator of claim 1 wherein said internal threaded surface of said upper control housing is contained within a ball nut.

6. The obturator of claim 1 wherein a first bore extends through said control shaft, and wherein said first and second spreading legs each form a portion of a second bore collinear with said first bore, for accommodating a guide pin through said control shaft and said first and second spreading legs.

7. The obturator of claim 1 wherein said control shaft has a knob to facilitate manual turning of the control shaft.

8. The obturator of claim 1 wherein each spreading leg further comprises:
   an upper portion having an insertion tang; and
   a lower spreading leg portion having an insertion slot for interfitting with said insertion tang.

9. An obturator and working tube kit for performing a surgical procedure at a location in a patient's body comprising the obturator of claim 1 and a working tube.

* * * * *